(12) United States Patent
White et al.

(10) Patent No.: US 7,588,572 B2
(45) Date of Patent: *Sep. 15, 2009

(54) CONNECTOR FOR DOMED CUTTING TOOL

(75) Inventors: Patrick M. White, Downingtown, PA (US); Meyer Fishbein, West Borough, MA (US)

(73) Assignee: Greatbatch Medical S.A. (CH)

( * ) Notice: Subject to any disclaimer, the term of this patent is extended or adjusted under 35 U.S.C. 154(b) by 114 days.

This patent is subject to a terminal disclaimer.

(21) Appl. No.: 11/386,073

(22) Filed: Mar. 21, 2006

(65) Prior Publication Data

US 2006/0195110 A1     Aug. 31, 2006

Related U.S. Application Data

(63) Continuation of application No. 10/359,605, filed on Feb. 7, 2003, now Pat. No. 7,048,740, which is a continuation of application No. 09/671,234, filed as application No. PCT/US99/05951 on Mar. 18, 1999, now abandoned.

(51) Int. Cl.
*A61B 17/00* (2006.01)

(52) U.S. Cl. .......................... 606/80; 606/81

(58) Field of Classification Search ............... 606/80, 606/79, 81, 83, 84, 85, 86, 96, 103, 104, 606/180; 407/42, 54, 61, 62, 91, 99; 408/231, 408/227, 239 R, 713; 404/62; 623/22.12, 623/908; 279/93, 79, 80, 145; 403/348, 403/349

See application file for complete search history.

(56) References Cited

U.S. PATENT DOCUMENTS

| | | | |
|---|---|---|---|
| 4,621,637 A | 11/1986 | Fishbein | |
| 5,462,548 A | 10/1995 | Pappas et al. | |
| 5,486,181 A * | 1/1996 | Cohen et al. | 606/91 |
| 5,658,290 A | 8/1997 | Lechot | |
| 5,976,144 A | 11/1999 | Fishbein et al. | |
| 5,980,170 A * | 11/1999 | Salyer | 408/239 R |
| 6,102,915 A * | 8/2000 | Bresler et al. | 606/80 |
| 6,129,732 A | 10/2000 | Lechot | |
| 6,168,600 B1 | 1/2001 | Grace et al. | |
| 6,221,076 B1 | 4/2001 | Albrektsson et al. | |
| 6,250,858 B1 | 6/2001 | Salyer | |
| 6,409,732 B1 * | 6/2002 | Salyer | 606/91 |
| 6,475,221 B1 * | 11/2002 | White et al. | 606/80 |
| 6,854,742 B2 * | 2/2005 | Salyer et al. | 279/93 |
| 7,048,740 B2 * | 5/2006 | White et al. | 606/80 |

FOREIGN PATENT DOCUMENTS

| | | |
|---|---|---|
| EP | 0 307 949 | 3/1989 |
| EP | 1 066 796 | 1/2001 |
| FR | 2542230 | 9/1984 |

* cited by examiner

*Primary Examiner*—Pedro Philogene
(74) *Attorney, Agent, or Firm*—Michael F. Scalise

(57) ABSTRACT

The surgical reamer has a hollow dome with apertures spaced apart arranged in arcs extending from an apex of the dome to the base portion of the dome, and removable teeth positioned in the apertures. Each cutting tooth has a flange that is aligned flush with the external surface of the dome, and a raised cutting edge extending above the flange and the external surface of the dome, and an interior passageway communicating between the outside and inside of the dome. In one embodiment, a base plate is removably secured on the base portion of the dome to provide closure of the central cavity of the dome.

10 Claims, 15 Drawing Sheets

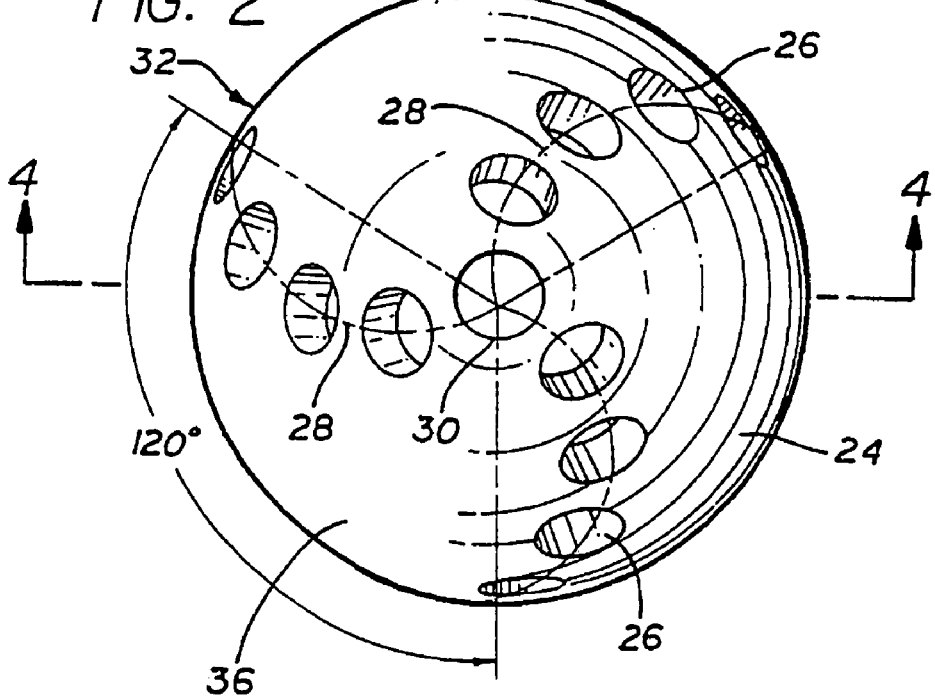
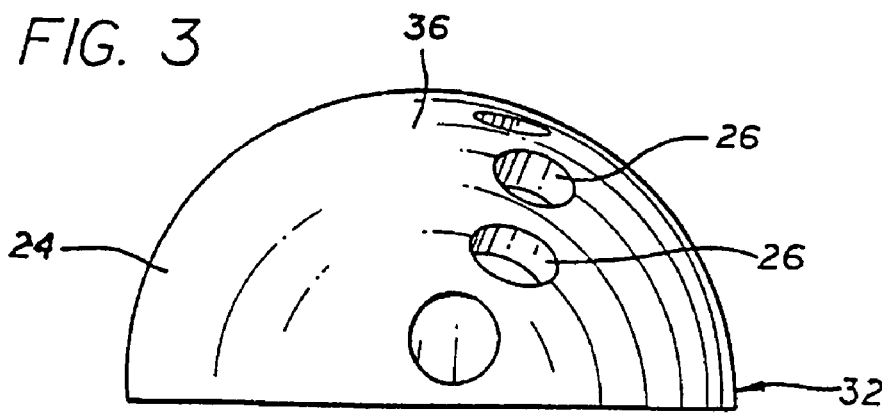

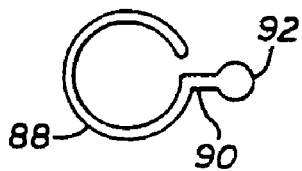
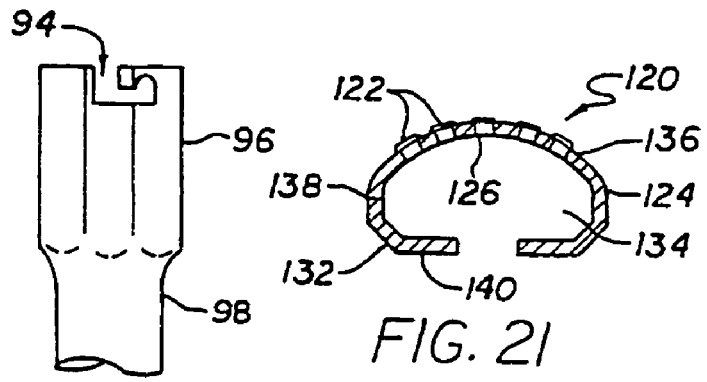
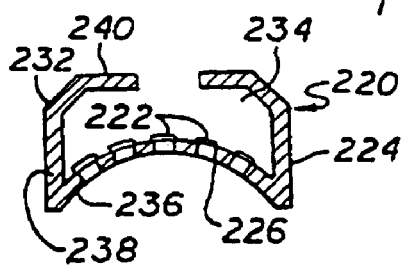
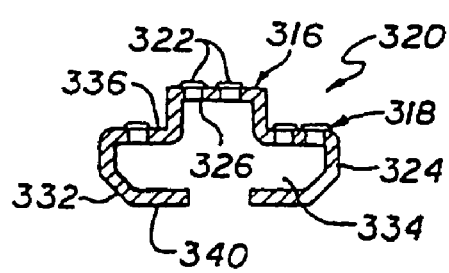
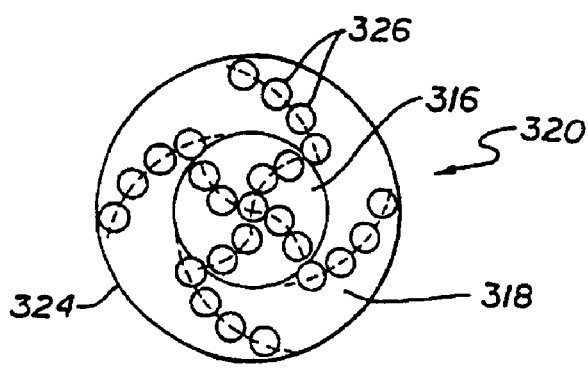

CONNECTOR FOR DOMED CUTTING TOOL

CROSS REFERENCE TO RELATED APPLICATIONS

This application is a continuation of U.S. patent application Ser. No. 10/359,605, filed Feb. 7, 2003, now U.S. Pat. No. 7,048,740, which is a continuation of U.S. patent application Ser. No. 09/671,234, filed Sep. 19, 2000, now abandoned, which is the U.S. national stage of international patent application No. PCT/US99/05951, filed Mar. 18, 1999, which claims priority to U.S. patent application Ser. No. 09/040,861, filed Mar. 18, 1998, now U.S. Pat. No. 5,976,144.

TECHNICAL FIELD

This invention relates generally to surgical devices, and more particularly concerns a rotatable surgical cutting tool for shaping a joint socket in preparation for receiving a joint prosthetic device.

BACKGROUND OF THE INVENTION

It is now common practice in the treatment of severe cases of arthritic and other forms of degenerative joint diseases, especially the hip, to shape the hip joint socket by removing diseased and eroded bone and cartilage to conform with the shape of a prosthetic device to be implanted. Prior to installing a hip joint prosthesis, for example, articular cartilage and bone is commonly removed from the socket to reshape the acetabulum to accurately match the dimensions of the prosthetic device to be implanted. In the past, the tissue and debris removed from the hip socket was discarded; however, more recently, it has become important to capture the debris for preservation and use later in the procedure.

It is generally desirable for milling devices and reamers used in preparing a joint socket for a prosthesis to have cutting edges that can cut through a wide variety of tissue, such as joint cartilage and bone tissue, ranging in density from the soft or porous tissue to the denser bone. The surgical tools with hollow cutting heads are more widely used than other more open designs, because hollow head devices allow tissue and other debris to be captured within the cutting head.

Two distinct types of hollow dome cutting tools are currently available that capture the debris. One type employs a slotted dome with adjacent blades that are shaped to generate a socket, when rotated, conforming to the shape and dimensions of the prosthesis to be implanted. The debris cut by the blades falls through slots in the dome.

In another type of surgical milling tool, commonly called a "grater" reamer, the milling cutters are formed on the body by upsetting the body around openings in the body, and sharpening selected edges of the upset portions of the body. The surgical milling tool has a body with a hemispherically-shaped outer surface, an internal cavity, and milling cutters formed out of the perforations in the body at spaced-apart locations on the outer surface. The tool can be rotated in a joint socket to mill the tissues of the joint socket, such as for preparation of the joint socket for a prosthesis. The perforations in the body communicate with the internal cavity which receives the debris. The milling cutters of the milling tool are formed as cup-shaped projections extending above the perforations that face in a direction of rotation, and are arranged in a series of arcs extending circumferentially around the body. The outer wall of the milling tool forming the cup-shaped cutting edge projections is relatively thin, resulting in reduced cutting accuracy. The milling tool and cutting edge projections are formed of sheet steel, which can become dull relatively rapidly during use. Typically, if the cutting surfaces are formed integrally with the shell, such as with raised cutting edges formed directly in the shell, the manufacturing of the devices becomes very costly. In addition, once the projections forming the cutting edges of the milling tool are dull, the entire milling tool is typically discarded.

An example of a grater type of reamer is shown in U.S. Pat. No. 5,658,290 to Lechot, which further provides radial rods on the underside of the reamer cap that join up at the center of the cap and are integral. A reamer spindle has a shank with a head equipped with a bayonet having a locking mechanism for securing the reamer. The center of the bayonet is recessed to receive the radial rods and serve as a cavity for debris.

It would be desirable to provide a reaming tool fabricated from heat treated machined metal components to provide greater cutting accuracy, and at lower manufacturing costs than conventional surgical cutters. In this regard it would be desirable to form the cutters of a hardened cutting material to provide superior cutting edges. In addition, it would be desirable to provide a reaming tool with replaceable cutting edges, so that once the cutting edges become dull, they can be removed, resharpened, and replaced, for improved economy of use and maintenance. The present invention meets these needs.

It would be further desirable to provide a reaming tool that not only captures debris passing through the teeth, but one that also allows easier removal and use of the debris collected within the tool, versus currently available tools. The present invention is also an improved means for meeting this need.

SUMMARY OF THE INVENTION

Briefly, and in general terms, the present invention provides for an improved reaming tool that is fabricated from machined metal components to provide greater cutting accuracy, and at lower manufacturing costs than conventional cutters. The reaming tool has a multiplicity of cutters that can be formed of heat treated tool steel, to provide superior cutting edges. In addition, once the individual cutters become dull, they can readily be removed, replaced, and can even be resharpened and used again, for improved economy of use and maintenance.

The present invention accordingly provides for a rotary surgical reamer for removing bone and tissue from a joint to facilitate the installation of a prosthetic device. The rotary surgical reamer comprises a hollow reamer body, the hollow reamer body having a base portion, a wall with a surface defining a central cavity and a plurality of spaced apart apertures through the wall at a plurality of spaced apart locations on the wall defining cutting sites. Means are provided for connecting the hollow reamer body to a source of rotary power, and a plurality of teeth are removably disposed in the apertures. Each of the teeth have a tooth body having a base portion and a raised cutting edge, and the tooth body includes means for holding the tooth in a fixed position at one of the cutting sites. The tooth body also has a surface defining a passageway communicating between the external surface of the wall and the central cavity for passage of removed bone and tissue through the wall into the central cavity. In a currently preferred embodiment, the tooth body includes a flange for spacing the cutting edge a desired distance beyond the external surface of the wall of the reamer body. In one presently preferred embodiment, the teeth have a generally tubular shape.

The hollow reamer body preferably has a shape with a central axis of rotation about which perpendicular cross-sectional cutting patterns are generated during rotation of the hollow reamer body, allowing the hollow reamer body to be rotated without wobbling. In one presently preferred embodiment, the external surface of the hollow reamer body has a three-dimensional contour that is generally hemispherical, although the hollow reamer body may also have a three-dimensional contour selected from the group consisting of generally spherical, oblate spheroid, generally cylindrical, generally polygonal, or combinations thereof. Means for connecting the hollow reamer body to a source of rotary power is carried on the base portion of the hollow reamer body.

In one presently preferred embodiment, the external surface of the hollow reamer body has a three-dimensional contour having an apex, and the plurality of cutting sites are spaced apart in an arcuate array extending from a site adjacent the apex toward the base portion of the hollow reamer body, forming a helical pattern. In another presently preferred embodiment, the cutting sites are arranged in a plurality of arcs extending from a site adjacent to an apex of the hollow reamer body to the base portion.

In another preferred aspect of the invention, the rotary surgical reamer includes closure means adapted to be secured to the base portion of the hollow reamer body. In a presently preferred embodiment, the closure means comprises a base plate removably disposed on the base portion of the hollow reamer body and means for securing the base plate to the base portion of the hollow reamer body for closure of the central cavity of the hollow reamer body. The internal surface of the central cavity preferably defines at least one inner annular groove, and the means for securing the base plate to the base portion of the hollow reamer body comprises a retaining spring having first and second ends and having a relaxed bent configuration and a compressed configuration in which the ends of the retaining spring can be extended into the inner annular groove of the base portion of the hollow reamer body.

A drive shaft is also provided for transmitting torque for rotation of the hollow reamer body, the retaining spring having a surface defining a central aperture for receiving the drive shaft, and the base plate having a surface defining a central aperture for receiving the drive shaft for transmitting torque for rotation of the hollow reamer body. The drive shaft has a terminal end that is press fit into the central aperture in the base plate, and the terminal end of the drive shaft has a transverse aperture in the shaft, and a retaining pin adapted to be received in the transverse aperture that when received in the transverse aperture extends above the surface of the shaft, for securing the drive shaft to the base plate.

In one currently preferred embodiment, the means for securing the base plate to the base portion of the hollow reamer body includes a retaining spring having a relaxed bent configuration and a compressed, substantially flat configuration in which the terminal ends of the retaining spring can be extended into the inner annular groove of the base portion of the hollow reamer body. The retaining spring also preferably has a central aperture with a notch to allow the drive shaft to pass through the retaining spring.

A tubular collar is provided for securing the retaining spring in the compressed configuration. The tubular collar is provided with a keyway for receiving a retaining pin inserted in the shaft, such that the tubular collar can be placed over the shaft and pressed against the retaining spring and rotated to lock the pin in the collar in a position pressing against the retaining spring, so that the retaining spring is locked in the flattened configuration.

In an alternate preferred embodiment, the hollow reamer body comprises a hollow can having a base portion, a wall with a top surface and an internal surface defining a central cavity and a plurality of spaced apart cutting sites on the wall. The hollow can has a central axis of rotation about which perpendicular cross-section cutting patterns are generated upon rotation of the hollow can, allowing the hollow can to be rotated without wobbling. The base portion of the hollow can also preferably includes means for connecting the hollow can to a source of rotary power. In this embodiment, the plurality of cutting sites comprises a site located adjacent to the axis of the can, with a plurality of sites arrayed in a plurality of arcs extending on the top surface of the can from the axis of the can to the edge of the top surface.

In another general aspect of the invention, a rotary surgical reamer comprises a hollow reamer body having a wall with an external surface and a periphery, the wall defining a central cavity and a plurality of spaced apart apertures through the wall at a plurality of spaced apart locations on the wall defining cutting sites. The cutting sites define passageways communicating between the external surface of the wall and the central cavity for passage of removed bone and tissue through the wall into the central cavity. A single mounting bar extends diametrically across and is affixed to a back side of the periphery, the mounting bar having means for attaching a powered rotary driver thereto.

In yet another general aspect of the invention, a rotary surgical reamer comprises a hollow reamer body having a wall with an external surface and a periphery, the wall defining a central cavity and a plurality of spaced apart apertures through the wall at a plurality of spaced apart locations on the wall defining cutting sites. The cutting sites define passageways communicating between the external surface of the wall and the central cavity for passage of removed bone and tissue through the wall into the central cavity. A pair of parallel mounting bars extend chordally across and are affixed to a back side of the periphery, the mounting bars having means for attaching a powered rotary driver thereto.

In still another general aspect of the invention, a rotary surgical reamer comprises a hollow reamer body having a wall with an external surface and a periphery, the wall defining a central cavity and a plurality of spaced apart apertures through the wall at a plurality of spaced apart locations on the wall defining cutting sites. The cutting sites define passageways communicating between the external surface of the wall and the central cavity for passage of removed bone and tissue through the wall into the central cavity. Removable teeth are located at substantially all of the cutting sites. An array of three radial mounting bars extend inwardly from and are affixed to a back side of the periphery, the mounting bars having means for attaching a powered rotary driver thereto.

These and other aspects and advantages of the invention will become apparent from the following detailed description and the accompanying drawings, which illustrate by way of example the features of the invention.

BRIEF DESCRIPTION OF THE DRAWINGS

FIG. 2 is a top plan view of the hollow dome reamer of FIG. 1;

FIG. 3 is a side elevational view of the hollow dome reamer of FIG. 1;

FIG. 19, is a plan view of a ring lock spring adapted to be received on the annular groove of the drive shaft;

FIG. 20 is a partial view of a hollow drive rod adapted to fit over the drive shaft and ring lock spring;

FIG. 21 is a sectional view of an alternate embodiment of a hollow reamer body of the hollow dome reamer of the invention having a shape for use as a glenoid reamer;

FIG. 22 is a sectional view of another alternate embodiment of a hollow reamer body of the hollow dome reamer of the invention having an inverted curved shape for use as a femur or glenoid reamer;

FIG. 23 is a sectional view of another alternate embodiment of a hollow reamer body of the hollow dome reamer of the invention having a tiered shape with flattened shoulders for use as a patella recessing tool;

FIG. 24 is a top plan view of the hollow reamer body of FIG. 23 showing the pattern of the cutting teeth;

DETAILED DESCRIPTION OF THE PREFERRED EMBODIMENT(S)

Figure 1:
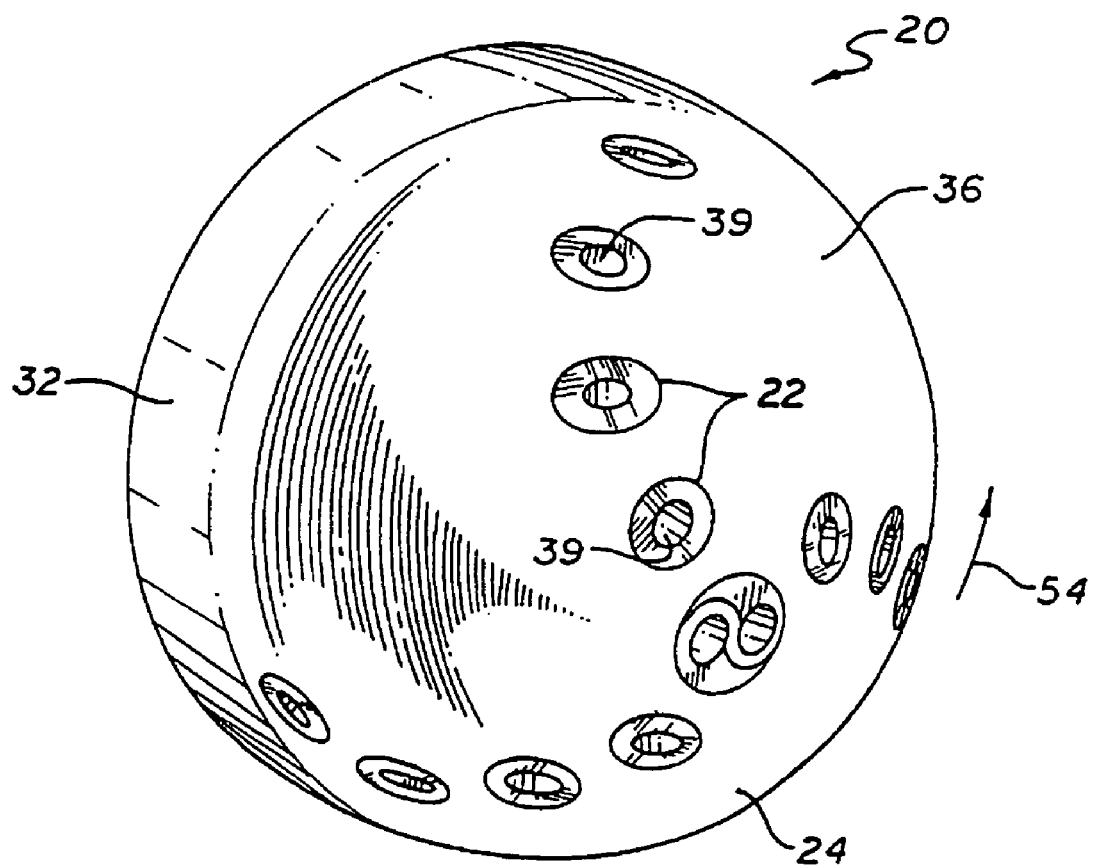
FIG. 1 is a perspective view of an hollow dome reamer with removable, replaceable cutters according to the present invention.

During surgery for preparation of a joint for installation of a joint prosthesis, it has become important to capture and preserve the tissue and debris removed from a joint for later use. However, conventional surgical tools with hollow cutting heads that are typically used for this type of surgery commonly have cup-shaped cutting edge projections that are relatively thin, become dull relatively rapidly during use, and are not readily sharpened or replaced, so that once the cutting edges of the surgical tool become dull, the surgical tool is useless.

As is illustrated in the drawings, the invention is accordingly embodied in a hollow dome reamer that provides greater cutting accuracy, with removable teeth having superior cutting edges. The removable teeth can readily be replaced, and resharpened for repeated usage. Referring to FIGS. 1 through 11, the hollow dome reamer 20 is preferably a rotary surgical reamer having a plurality of inserted modular teeth 22 or cutters that are removably disposed in a hollow reamer body or dome 24 having a plurality of apertures 26 formed therein spaced apart at various locations around the dome. In one presently preferred embodiment, the dome has a hemispherical shape, although other three dimensional geometrical shapes may also be desirable and suitable for different applications, and in general the dome may be shaped to be generally spherical, an oblate spheroid, generally cylindrical, generally polygonal, and combinations thereof. The dome is also advantageously shaped to have a central axis of rotation about which perpendicular cross-sectional cutting patterns are generated during rotation of the hollow reamer body, allowing the hollow reamer body to be rotated without wobbling. In a presently preferred embodiment, the teeth are tubular, and the apertures are correspondingly cylindrical to accept the tubular teeth, but other geometrical shapes of the teeth and the apertures may also be suitable. The apertures of the dome and the tubular teeth are currently preferably dimensioned so that the tubular teeth can be press fit into the apertures in the dome; although threading the tubular teeth and the apertures to have corresponding threads to allow the tubular teeth to be threadedly secured in the dome, and other similar ways of securing the tubular teeth in the cylindrical apertures of the dome may also be suitable.

As can best be seen in FIGS. 2, 3, 5, 7 and 8, the apertures are preferably arranged in a plurality of arcs 28 extending from an apex 30 of the dome to the base portion 32 of the dome. In one presently preferred embodiment illustrated in FIGS. 1 to 5 and 7, a tubular cutter or tooth is provided in an apex aperture located off-center at the apex of the dome, with tubular teeth being provided in a series of three equally spaced arcs of spaced apart apertures, each of the arcs commencing at the center of the apex aperture and extending to the periphery of the base portion, with the apertures in the arcs being regularly spaced apart at pre-determined distances along the arcs. In this embodiment, there are currently preferably three equally spaced arcs, with three regularly spaced apertures in each arc, but greater numbers of arcs may also be suitable.

Figure 8:
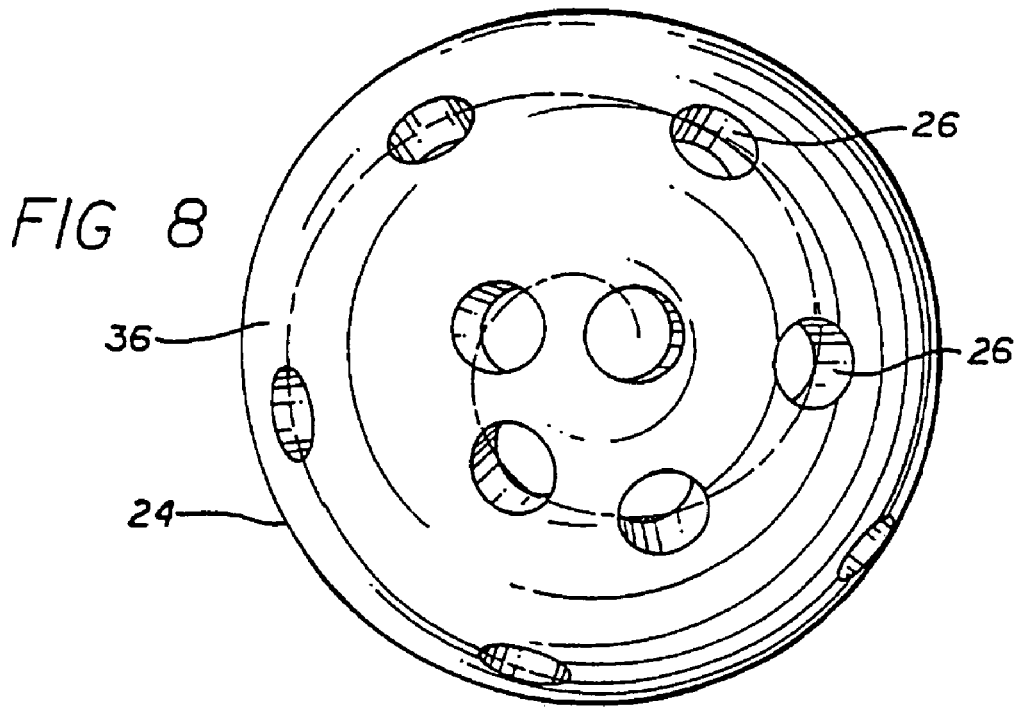
FIG. 8 is a schematic diagram of an alternate pattern of placement of the cutters of the hollow dome reamer.

In an alternative preferred embodiment illustrated in FIG. 8, a tubular tooth is provided in an apex aperture located adjacent to the apex of the dome, with tubular teeth being provided in an arcuate, generally helical path of spaced apart apertures, the arc commencing generally at the apex of the dome and extending to the periphery of the base portion. The apertures in the helical arc are preferably spaced apart at pre-determined distances along the arcs such that all of the apertures fall on a spiral line extending from the apex aperture of the dome to the periphery of the base portion.

Figure 4:
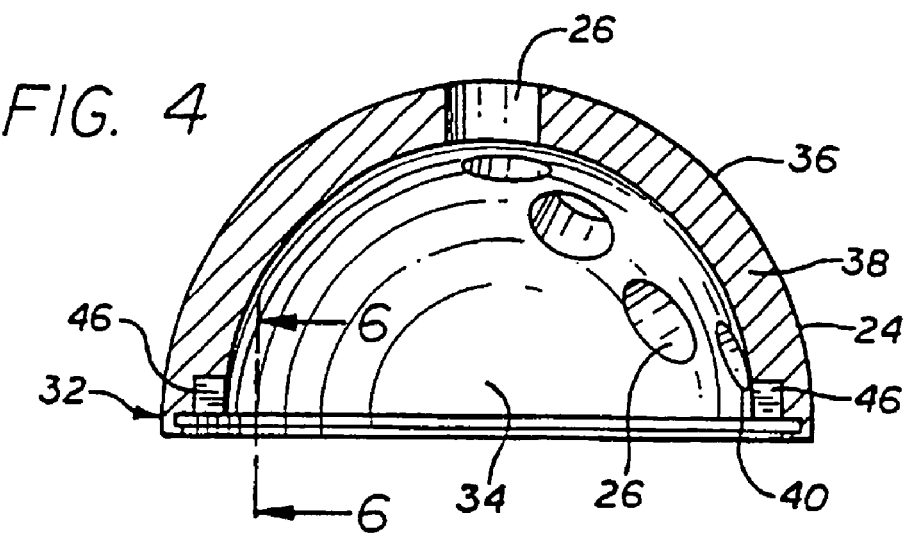
FIG. 4 is a cross-sectional view of the hollow dome reamer taken along line 4—4 of FIG. 2.
Figure 5:
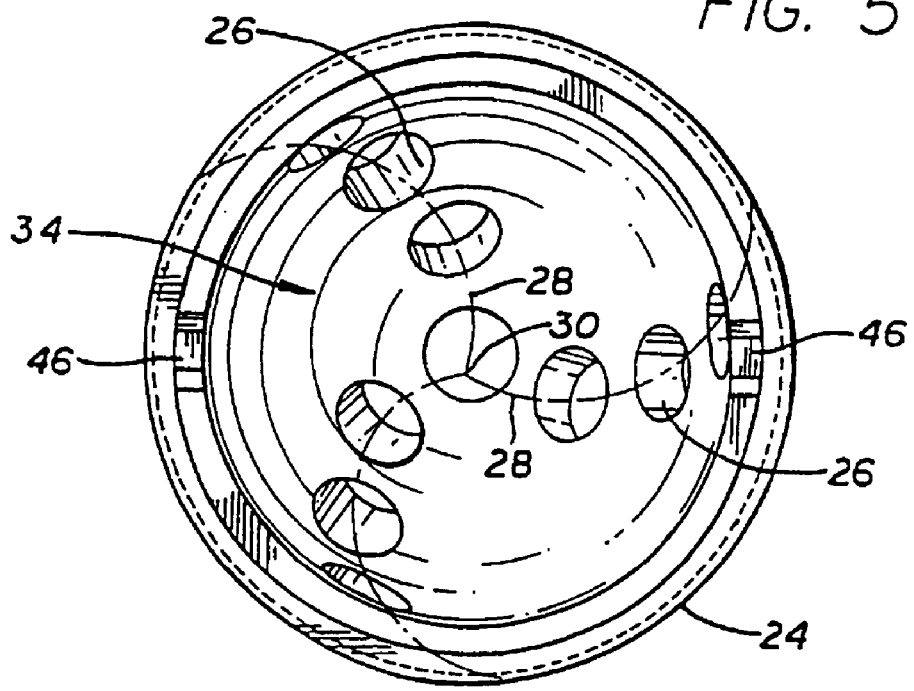
FIG. 5 is a bottom plan view of the hollow dome reamer of FIG. 1.
Figure 6:
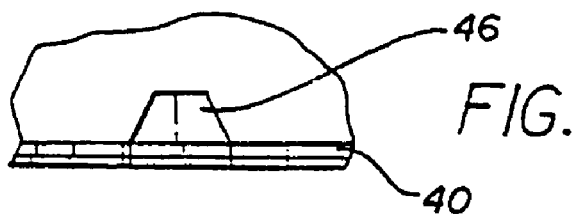
FIG. 6 is a side elevational view of a portion of the hollow dome reamer taken along line 6—6 of FIG. 4.
Figure 7:
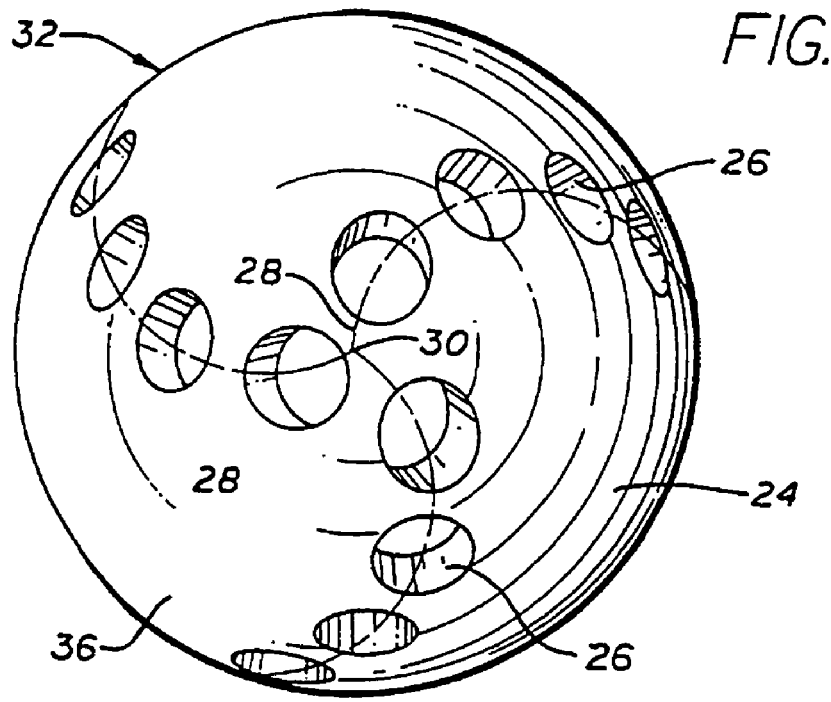
FIG. 7 is a schematic diagram of a pattern of placement of the cutters of the hollow dome reamer.

Referring to FIGS. 4 and 5, the dome has an inner central cavity 34 or chamber, a hemispherical external surface 36, and an outer wall 38 having a thickness that is sufficient to provide adequate support for a plurality of the tubular teeth disposed in the apertures of the dome. Each tubular tooth preferably also has an interior passageway 39, so that when the teeth are inserted in the apertures of the dome, the hollow tubular teeth provide communication between the external and internal areas of the dome through the wall. As explained above, while the teeth are currently preferably tubular, and the apertures are cylindrical, other cross-sectional shapes of the teeth and apertures may also be suitable as long as an interior passageway is provided in the teeth, and the teeth can be removably disposed in the apertures of the dome.

The base portion of the dome preferably has at least one inner annular groove 40 that can be seen in FIG. 4, for receiving the terminal ends 42 of a retaining spring 44 of the base plate, and a plurality of notches 46 adapted to receive corresponding key flanges 48 of the base plate, described below. In one presently preferred embodiment, the base portion of the dome has two diametrically opposed notches adapted to receive corresponding key flanges of the base plate. The dome is currently preferably formed from metal, such as steel, such as stainless steel or tool steel for example, titanium alloy, aluminum, aluminum alloy, nitinol, and molybdenum, although the dome can be made of other suitable materials, such as ceramic or plastic, for example.

Figure 9:
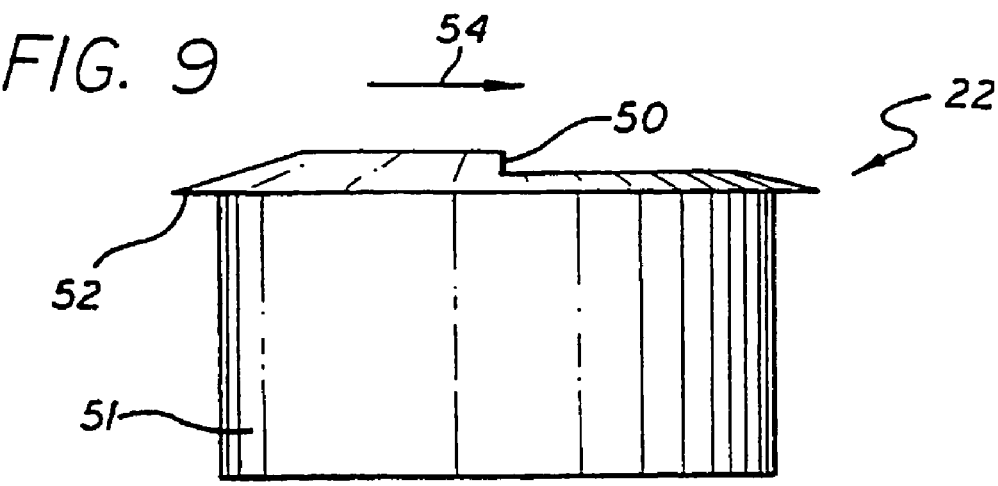
FIG. 9 is a side elevational view of a cutter of the hollow dome reamer of FIG. 1 according to the invention.
Figure 10:
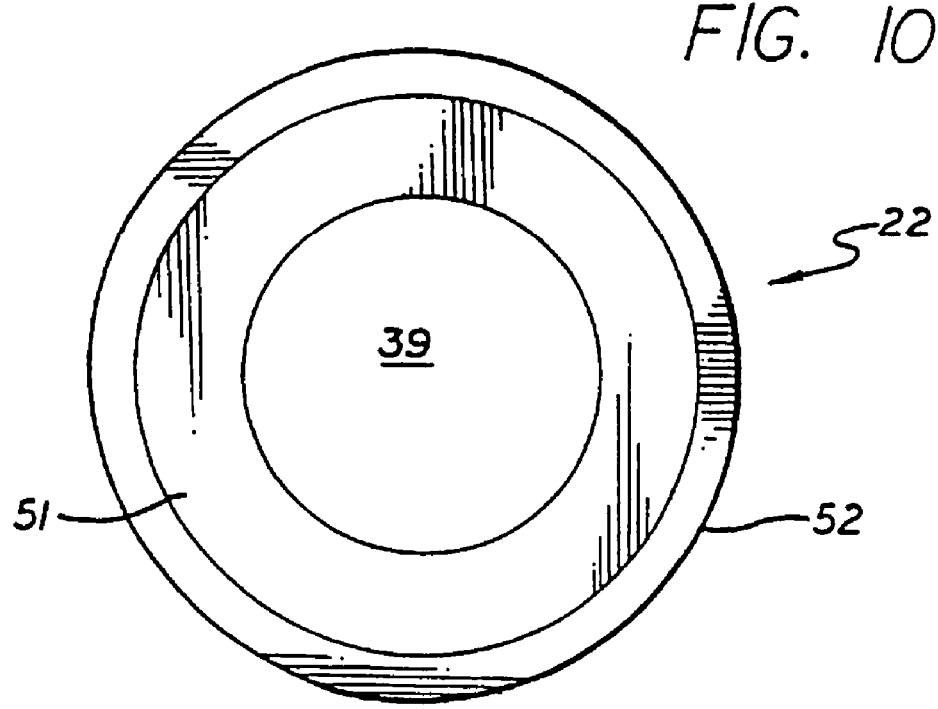
FIG. 10 is a bottom plan view of the cutter of FIG. 9.
Figure 11:
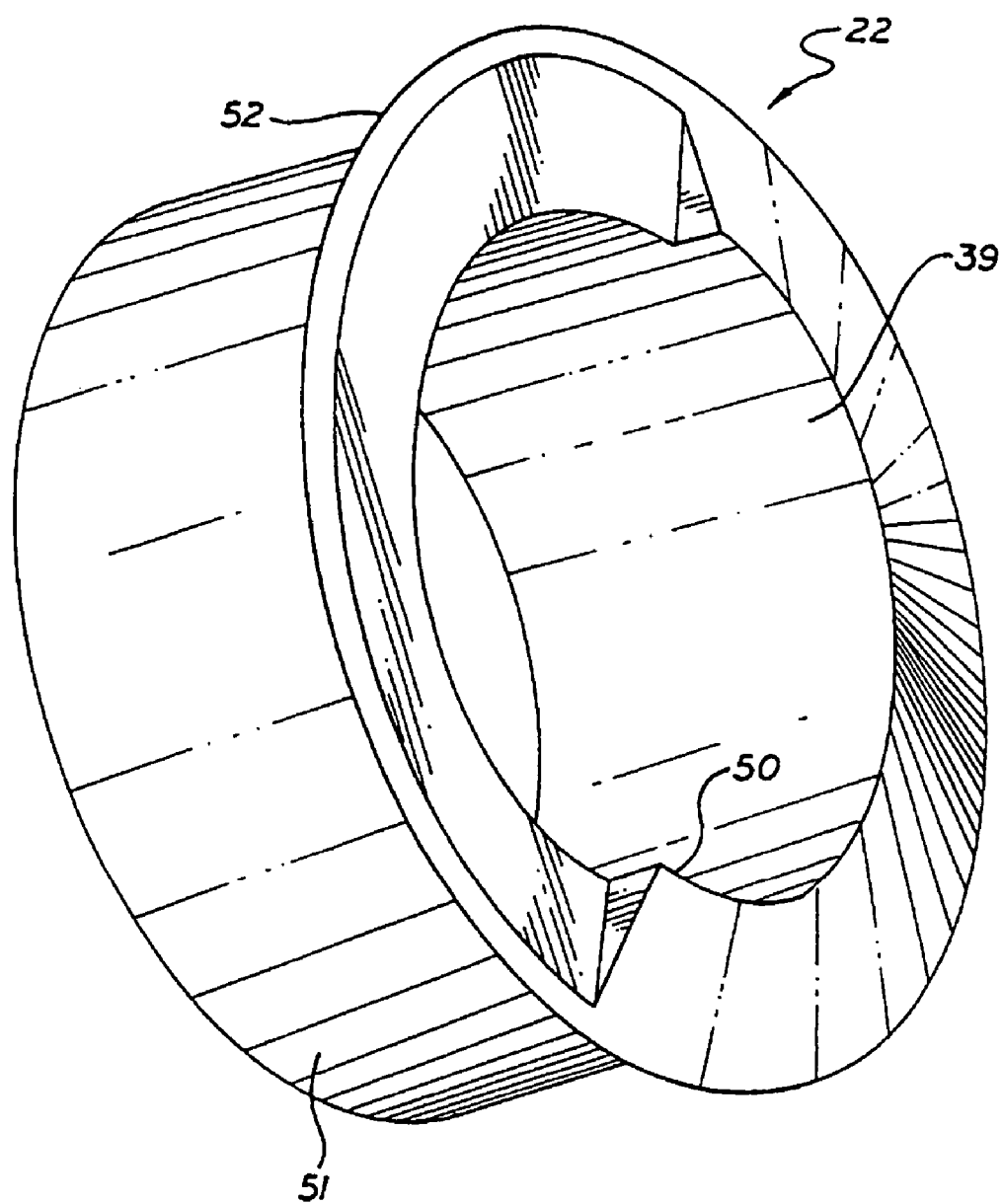
FIG. 11 is a perspective view of the cutter of FIG. 9.

As can best be seen in FIGS. 9 and 11, the tubular teeth each have a raised cutting edge 50, a tubular base portion 51, and a flange 52 or shoulder that is aligned with the hemispherical external surface of the dome to position the cutting edges of the teeth at a specific desired distance above or beyond the hemispherical external surface of the dome. The teeth are currently preferably fabricated of heat treated tool steel, although the teeth can also be formed from other suitable materials, such as stainless steel, ceramic, plastic, titanium alloy, aluminum alloy, nitinol, and molybdenum. Each cylindrical, tubular tooth insert is preferably formed by cutting a tube formed of tool steel into segments, and grinding down a portion of one end of a segment to form the flange or shoulder, and leaving the raised portion of the end of the segment as the cutting edge. The cylindrical, tubular tooth insert is then press fit in an aperture of the dome, oriented so that the flange is flush with the external surface of the dome and facing in a direction of rotation 54 of the dome, so that when the dome is rotated in the specified direction, the raised circular cutting edge section will perform the cutting of bone and other tissue, which will then be extruded through the central hole or passageway 39 in the tooth and into the central cavity of the dome.

Figure 12:
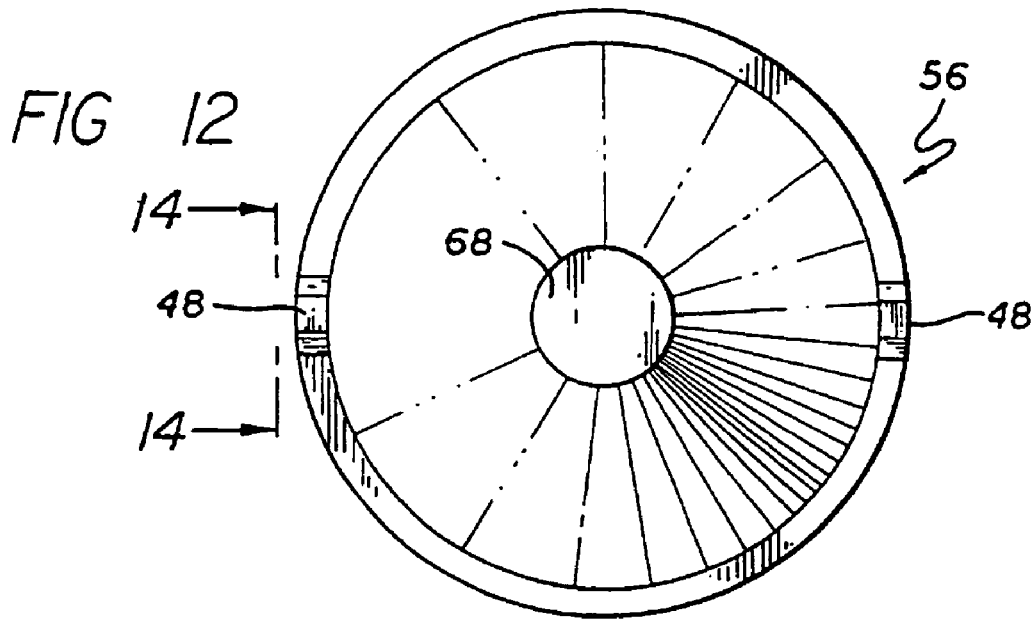
FIG. 12 is a bottom plan view of the base plate and drive shaft of the hollow dome reamer of FIG. 1 according to the invention.
Figure 13:
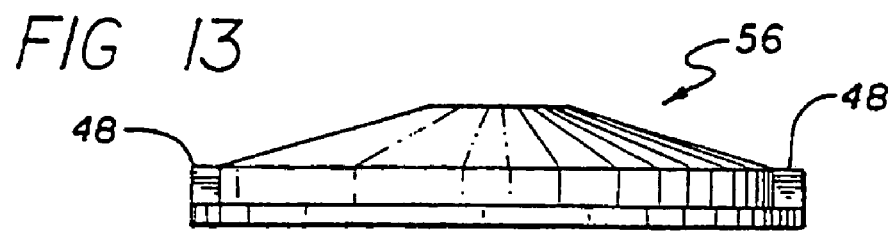
FIG. 13 is a side elevational view of the base plate of FIG. 12, shown without the drive shaft, for the sake of simplicity.
Figure 14:
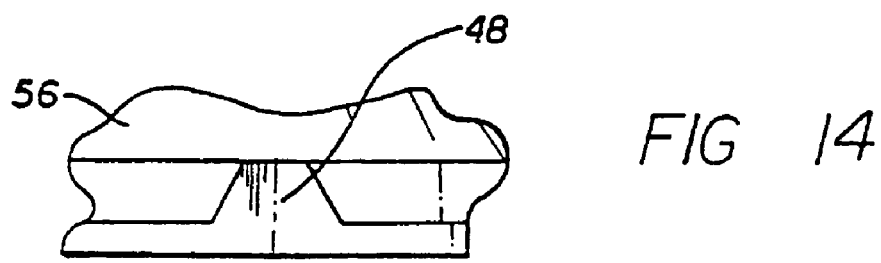
FIG. 14 is a side elevational view of a portion of the base plate taken along line 14—14 of FIG. 12, showing a key flange corresponding to the notches in the dome.

With reference to FIGS. 12 to 14, the hollow dome reamer also includes a circular base plate 56 with a plurality of key flanges 48 adapted to be received in the corresponding notches 46 of the base portion of the dome. The base plate is removably disposed on the base portion of the dome, and achieves closure of the central cavity of the dome. In a currently preferred embodiment, the circular base plate has a pair of diametrically opposed key flanges, and means 58 for securing the base plate to the base portion of the dome.

Figure 17:
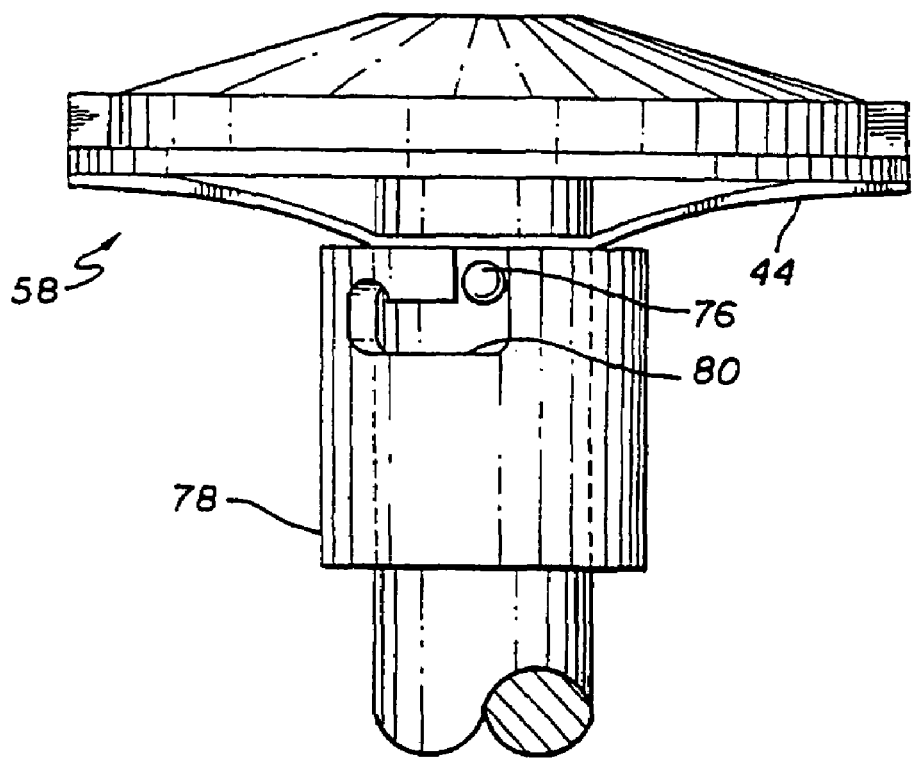
FIG. 17 is another side elevational view of the base plate and drive shaft of the hollow dome reamer of FIG. 1 showing the placement of a retaining spring over the drive shaft and retaining pin according to the invention.
Figure 18:
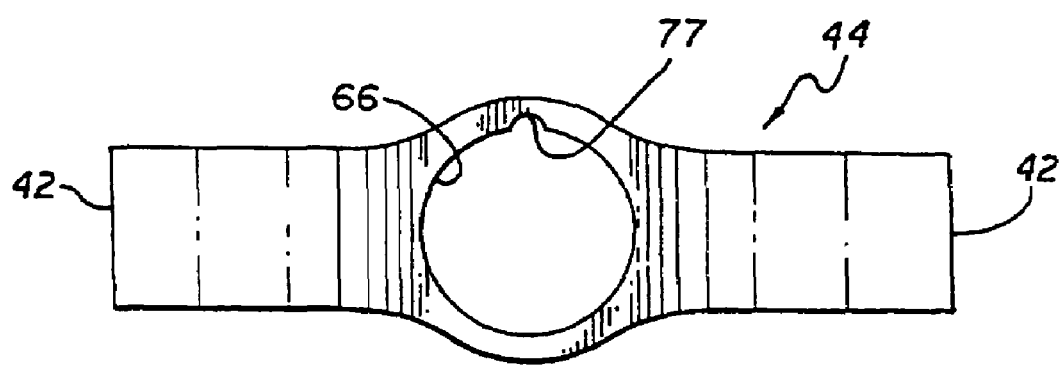
FIG. 18 is a plan view of the retaining spring of FIG. 17 according to the invention.
Figure 25:
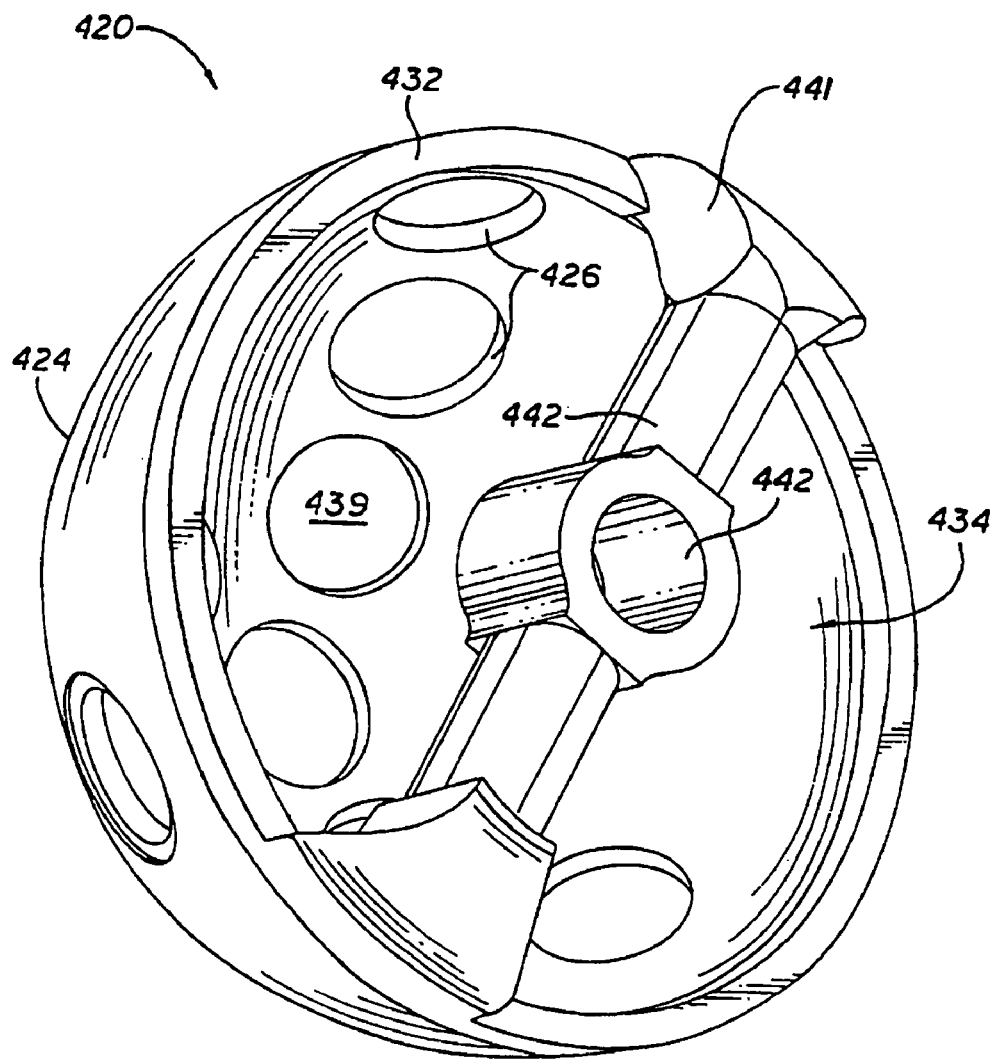
FIG. 25 is an external perspective view of the underside of a reamer having a single peripherally emanating mounting bar, according to the invention.
Figure 26:
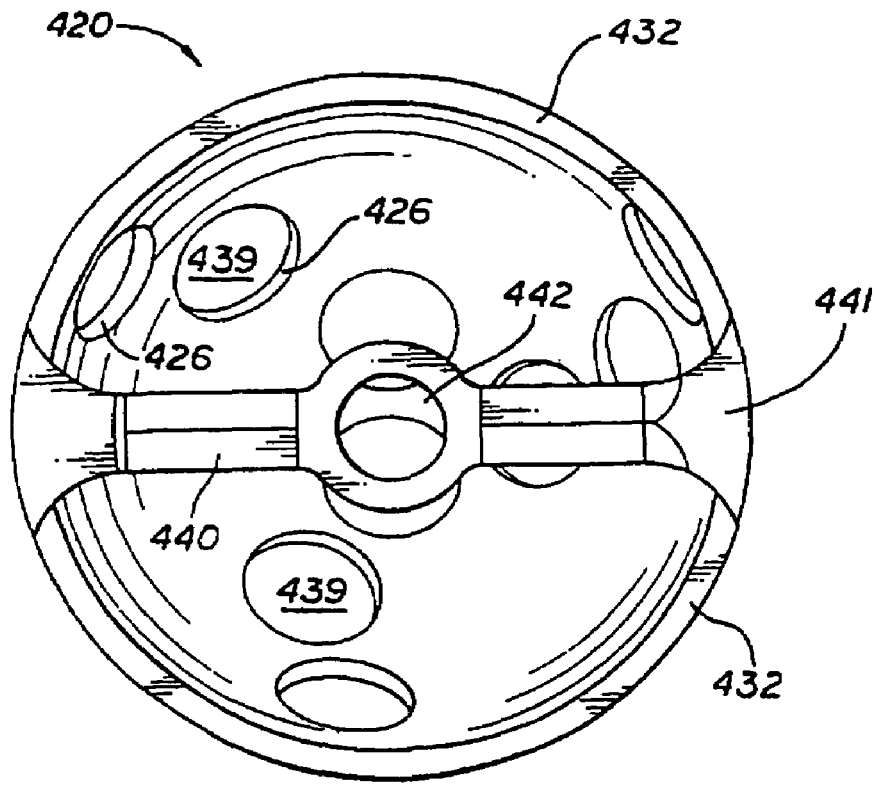
FIG. 26 is a bottom view of the reamer of FIG. 25.

In a currently preferred embodiment, the means for securing the base plate to the base portion of the dome comprises a leaf spring retaining spring 44 shown in FIGS. 17 and 18 that has a compressed, considerably flattened configuration in which the terminal ends of the retaining spring can be extended into the inner annular groove 40 of the base portion of the dome, and a relaxed, slightly bent configuration illustrated in FIG. 17 in which the terminal ends of the retaining spring do not extend into the inner annular groove of the base portion of the dome. The retaining spring preferably has a central aperture 66 to allow passage of a drive shaft, shown in FIGS. 15 and 17, through the retaining spring, and the circular base plate also has a central aperture 68 for receiving the drive shaft. The drive shaft 70 is provided for transmitting torque for rotation of the dome. The drive shaft has a terminal end 72 that is press fit into the aperture 68 in the base plate. The terminal end 72 of the shaft also has an aperture 74 for receiving a retaining pin 76 that, when received in the aperture of the terminal end of the drive shaft, extends above the surface of the drive shaft, for securing the drive shaft to the base plate. The retaining spring central aperture also includes a notch 77 to allow the retaining spring to slide over the retaining pin 76 of the drive shaft.

Figure 16:
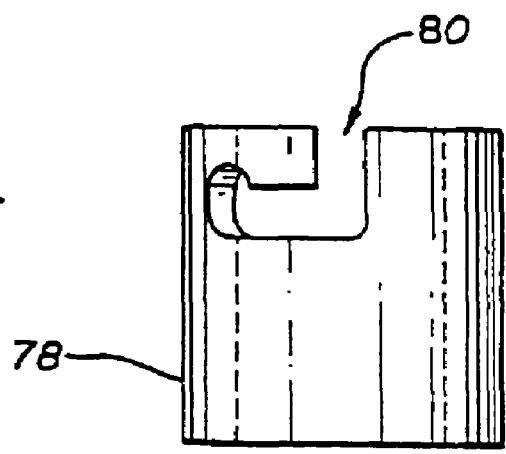
FIG. 16 is a side elevational view of a retaining collar for compressing the retaining spring to engage the inner annular groove of the dome, according to the invention.

Referring to FIGS. 16 and 17, a tubular collar 78 having a keyway 80 for receiving the pin of the shaft is also provided that fits over the drive shaft. The collar can be pressed against the retaining spring to flatten it, and then rotated to lock the pin in the keyway of the collar, so that the retaining is locked in a flattened configuration.

Figure 15:
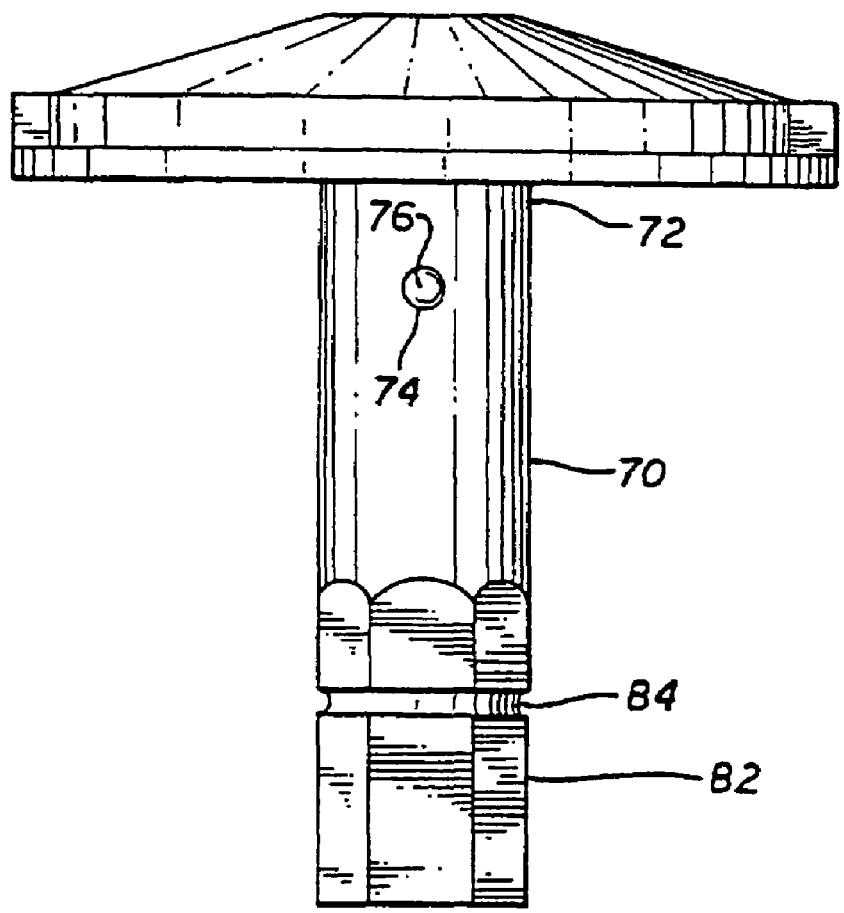
FIG. 15 is another side elevational view of the base plate and drive shaft of the hollow dome reamer of FIG. 1 showing the placement of a retaining pin according to the invention.

With reference to FIGS. 15 and 19, the proximal end 82 of the drive shaft also preferably has an annular groove 84 for receiving an annular spring lock 86 shown in FIG. 19. The spring lock comprises a main loop 88 that is received in the annular groove of the drive shaft, an arm 90 extending generally perpendicular to the curve of the loop, and a ball tip 92 at the distal end of the arm. Referring to FIG. 20, the arm and ball tip of the spring lock are adapted to be received in a slot 94 of a slotted collar 96 of a hollow drive rod 98, adapted to be connected to a source of rotary drive power, such as an electric drill motor.

FIG. 21 illustrates a first variant of the shape of the hollow reamer body illustrated in FIGS. 1-8, adapted for use as a glenoid reamer. In this variant, the shape of the external cutting surface of the hollow reamer body can be generally convex. but not necessarily hemispherical, and is similar in many respects to the embodiment illustrated in FIGS. 1-8, so that elements of the first variant that are similar to those of the first embodiment described above are described with similar reference numbers. The convex hollow dome glenoid reamer 120 preferably has a plurality of inserted modular teeth 122 that are removably disposed in the hollow reamer body or dome 124 having a plurality of apertures 126 formed therein spaced apart at various locations around the dome. The dome of the glenoid reamer is shaped to have a central axis of rotation about which perpendicular cross-sectional cutting patterns are generated during rotation of the hollow reamer body, allowing the hollow reamer body to be rotated without wobbling.

As was illustrated in FIGS. 1-5 and 7-8 in connection with the first embodiment, in the glenoid variant of the hollow dome reamer, the apertures are preferably arranged in a plurality of arcs extending from an apex of the dome to the base of the dome. Alternatively, a tubular tooth can be provided in an apex aperture located adjacent to the apex of the dome, with tubular teeth being provided in an arcuate, generally helical path of spaced apart apertures, the arc commencing generally at the apex of the dome and extending to the periphery of the base portion.

The hollow reamer body or dome has an inner central cavity 134 or chamber, an external surface 136, and an outer wall 138 having a thickness that is sufficient to provide adequate support for a plurality of the tubular teeth disposed in the apertures of the dome. The cutting teeth are as described hereinabove. As explained above, while the teeth are currently preferably tubular, and the apertures are cylindrical, other cross-sectional shapes of the teeth and apertures may also be suitable as long as an interior passageway is provided in the teeth, and the teeth can be removably disposed in the apertures of the dome. The base portion 132 of the dome preferably has an integral base plate 140 having an aperture for receiving a drive shaft for supplying rotary power to the reamer.

In another presently preferred variant of the hollow reamer body illustrated in FIG. 22, the shape of the hollow reamer body is adapted for use as a femur or glenoid reamer. In this second variant, the shape of the external cutting surface of the hollow reamer body can be generally concave, but not necessarily hemispherical, and is similar in many respects to the embodiment illustrated in FIG. 21, so that elements of this second variant that are similar to those described above are described with similar reference numbers. The hollow dome glenoid reamer 220 preferably has a plurality of inserted teeth 222 that are removably disposed in the hollow reamer body or dome 224 having a plurality of apertures 226 formed therein spaced apart at various locations around the dome. The dome of the concave femur or glenoid reamer is shaped to have a central axis of rotation about which perpendicular cross-sectional cutting patterns are generated during rotation of the hollow reamer body, allowing the hollow reamer body to be rotated without wobbling.

As was illustrated in FIGS. 1-5 and 7-8 in connection with the first embodiment, in the glenoid variant of the hollow dome reamer, the apertures are preferably arranged in a plurality of arcs extending from an apex of the dome to the base of the dome. Alternatively, a tubular tooth can be provided in an apex aperture located adjacent to the apex of the dome, with tubular teeth being provided in an arcuate, generally helical path of spaced apart apertures, the arc commencing generally at the apex of the dome and extending to the periphery of the base portion.

The hollow reamer body or dome has an inner central cavity 234 or chamber, an external surface 236, and an outer wall 238 having a thickness that is sufficient to provide adequate support for a plurality of the tubular teeth disposed in the apertures of the dome. The cutting teeth are as described hereinabove. As explained above, while the teeth are currently preferably tubular, and the apertures are cylindrical, other cross-sectional shapes of the teeth and apertures may also be suitable as long as an interior passageway is provided in the teeth, and the teeth can be removably disposed in the apertures of the dome. The base portion 232 of the dome preferably has an integral base plate 240 having an aperture for receiving a drive shaft for supplying rotary power to the reamer.

In another presently preferred variant of the hollow reamer body illustrated in FIGS. 23 and 24, the shape of the hollow reamer body is adapted for use as a patella recessing tool. In this third variant, the shape of the external cutting surface of the hollow reamer body can be generally tiered to have two or three tiers for example. Referring to the specific embodiment shown in FIGS. 23 and 24, the patella recessing reamer provides a generally flat raised first inner tier 316, and a generally flat lower second tier 318. This embodiment is similar in many respects to the embodiments illustrated in FIGS. 21 and 22, so that elements of this third variant that are similar to those described above are described with similar reference numbers. The hollow dome patella recessing reamer 320 preferably has a plurality of inserted teeth 322 that are removably disposed in the hollow reamer body or dome 324 having a plurality of apertures 326 formed therein spaced apart at various locations around the dome. The dome of the tiered patella recessing reamer is shaped to have a central axis of rotation about which perpendicular cross-sectional cutting patterns are generated during rotation of the hollow reamer body, allowing the hollow reamer body to be rotated without wobbling.

As is shown in FIG. 24, in the patella recessing variant of the hollow dome reamer, the apertures are preferably arranged in a plurality of arcs extending from an apex of the dome to the base of the dome. Alternatively, a tubular tooth can be provided in an apex aperture located adjacent to the apex of the dome, with tubular teeth being provided in an arcuate, generally helical path of spaced apart apertures, the arc commencing generally at the apex of the dome and extending to the periphery of the base portion.

The hollow reamer body or dome has an inner central cavity 334 or chamber, an external surface 336, and an outer wall 338 having a thickness that is sufficient to provide adequate support for a plurality of the tubular teeth disposed in the apertures of the dome.

The cutting teeth are as described hereinabove. As explained above, while the teeth are currently preferably tubular, and the apertures are cylindrical, other cross-sectional shapes of the teeth and apertures may also be suitable as long as an interior passageway is provided in the teeth, and the teeth can be removably disposed in the apertures of the dome. The base portion 332 of the dome preferably has an integral base plate 340 having an aperture for receiving a drive shaft for supplying rotary power to the reamer.

It has thus been demonstrated that the present invention provides for a reaming tool that provides greater cutting accuracy, with tubular teeth superior cutting edges that can readily be removed, replaced, and resharpened for repeated usage. The tubular teeth can be simply and inexpensively manufactured from hardened tool steel. The present invention thus provides for an improved hollow dome reamer providing for improved economy of use and maintenance, and at lower manufacturing costs than other conventional hollow dome reamers.

It should be recognized that other patterns of the teeth on the dome may also be suitable, such as a random scattering of locations of the teeth on the dome, or a symmetrical balancing of locations of the teeth on the dome so that forces exerted on the dome would be generally balanced. Other suitable closure means also may alternatively be provided, such as by simply providing the circular base plate with peripheral threads adapted to interfit with corresponding threads on the inner base portion of the dome, with the direction of the threading being such that the base plate can be secured to the dome by rotating the base plate in the direction of rotation of the dome.

FIGS. 25-32 portray still other, general aspects of the invention. Specifically, FIGS. 25-26 and 30-32 show one of such embodiments, i.e., a rotary surgical reamer 420 comprises a hollow reamer body 24 having a domed shape with an apex 424, a wall 38 with an external surface 436 and a peripheral base 432, the wall defining a central cavity 434 and a plurality of spaced apart apertures 426 through the wall 38 at a plurality of spaced apart locations on the wall 38 defining cutting sites. The cutting sites define passageways 439 communicating between the external surface 436 of the wall and the central cavity 434 for passage of removed bone and tissue through the wall 38 into the central cavity. A single mounting bar/retaining member 440 extends diametrically across and is affixed to a back side of the peripheral base 432, the mounting bar/retaining member 440 having a centering structure 443 with radiused sides 445 centered on the mounting bar/retaining member 440. Portions of the radiused sides 445 extend beyond parallel side surfaces 447 of the retaining member 440, and are adapted for centering a powered rotary driver thereto via a corresponding centering structure 443'. For example, an aperture 442 and interfacing cylindrical surface of a shaft 464 represent a suitable centering structure and corresponding structure 443' combination, with the purpose of facilitating a bayonet-type connection between the reamer 420 and driver in a manner described below. Mourning bar/retaining member 440 may be molded with base 432, as shown by armatures 441 or the like which further aid in the connection mechanism.

Figure 27:
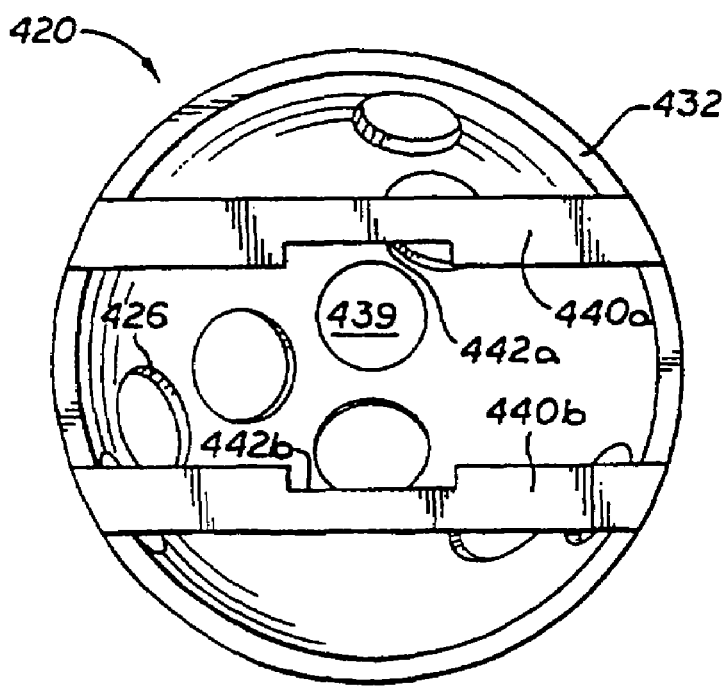
FIG. 27 is a bottom view of the underside of a reamer having a pair of peripherally emanating parallel mounting bars, according to the invention.
Figure 30:
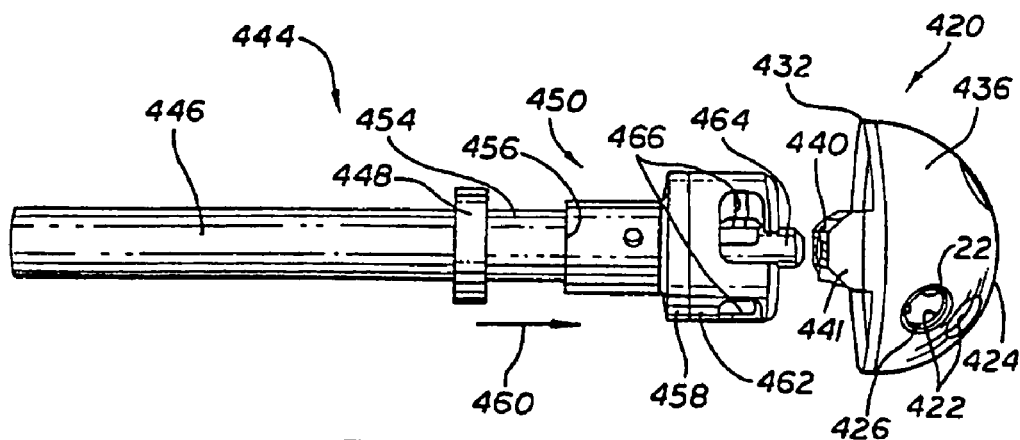
FIG. 30 is a side view of a preferred driver of the invention, shown with the reamer of FIGS. 25-26 prior to assembly.
Figure 31:
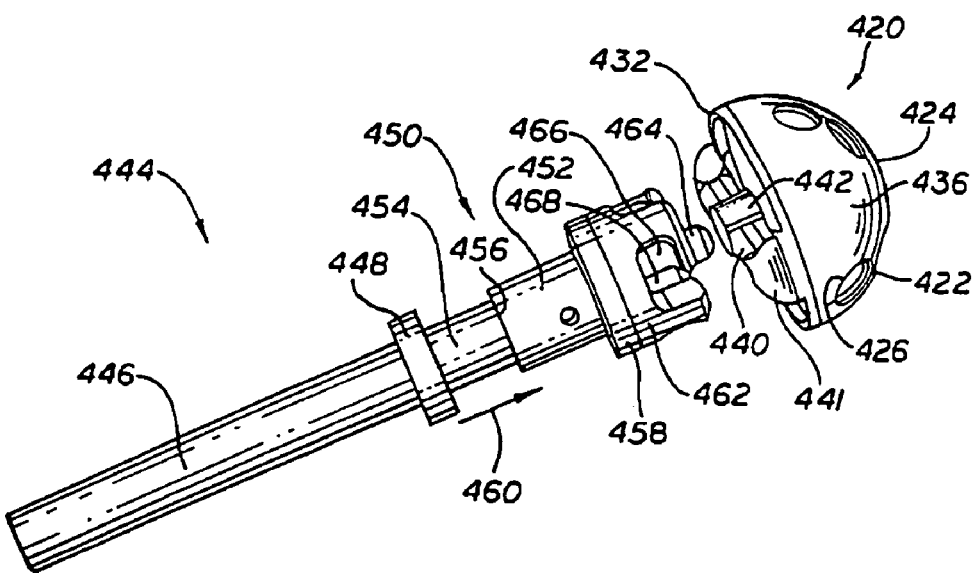
FIG. 31 is a perspective view of FIG. 30.
Figure 32:
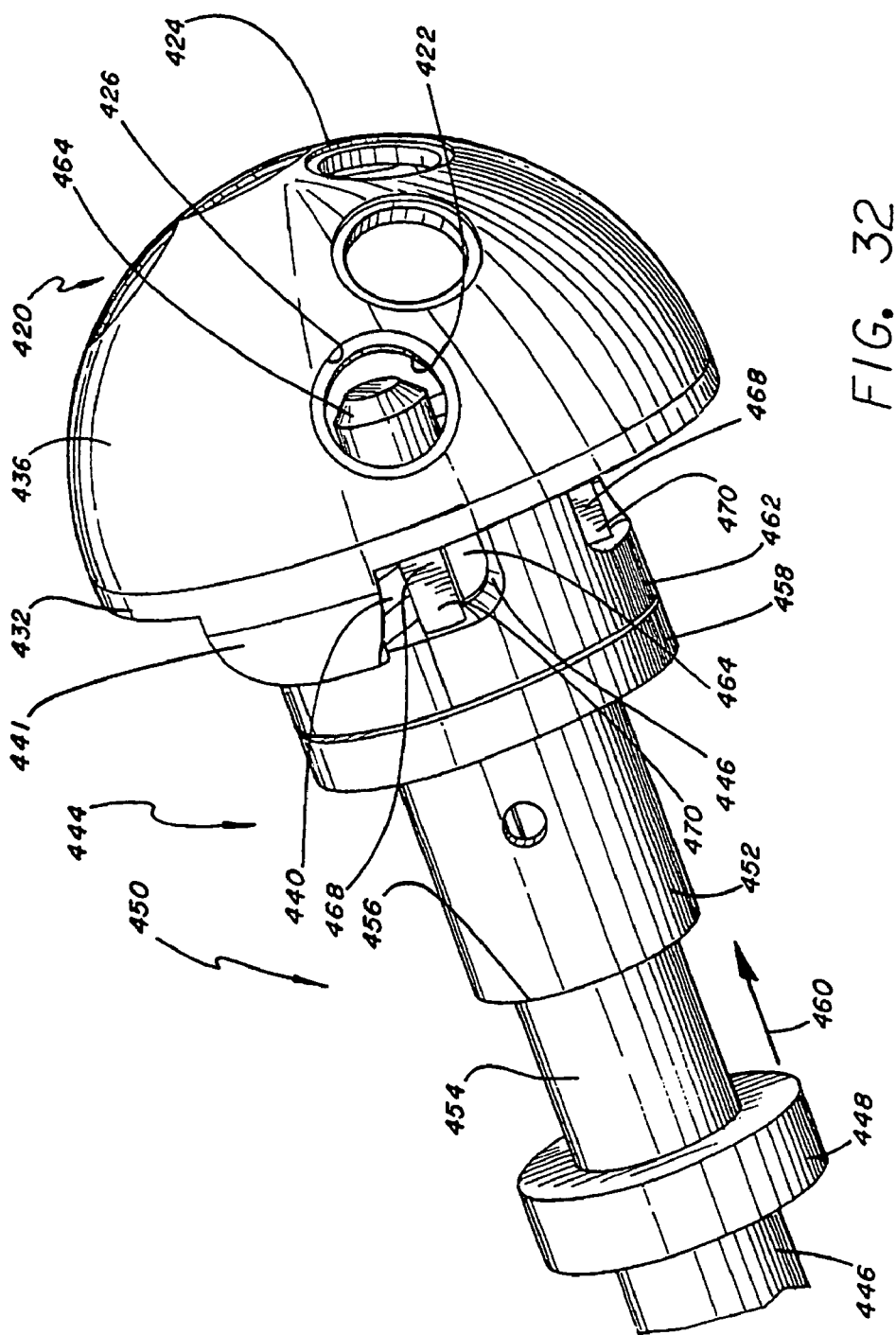
FIG. 32 is an enlarged perspective view of the driver and reamer dome of FIG. 30, shown assembled with one another.

Yet another general aspect of the invention is depicted in FIG. 27, where a pair of parallel mounting bars 440a-b extend chordally across and are affixed to a back side of the peripheral base, the mounting bars having means in the form of complementary notches 442a, 442b for centering a powered rotary driver (not shown) for connection to the reamer 420 in a manner that will be appreciated by those in the art from a discussion of FIGS. 30-32.

Figure 28:
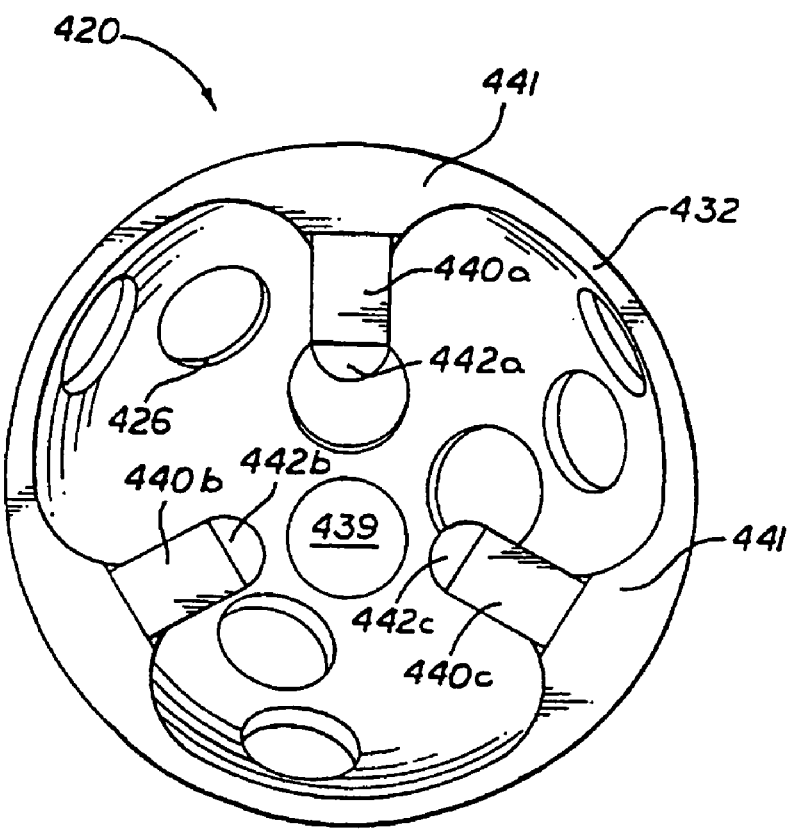
FIG. 28 is a bottom view of the underside of a reamer having a triangular array of peripherally emanating radial mounting bars, according to the invention.

Still another general aspect of the invention is shown in FIG. 28, where an array of three radial mounting bars 440a-c extend inwardly from and are affixed to a back side of the peripheral base 432, the mounting bars 440a-c respectively having central termini 442a-c spaced from one another which functions as a means for centering a powered rotary driver (not shown) during connection to the reamer.

Figure 29:
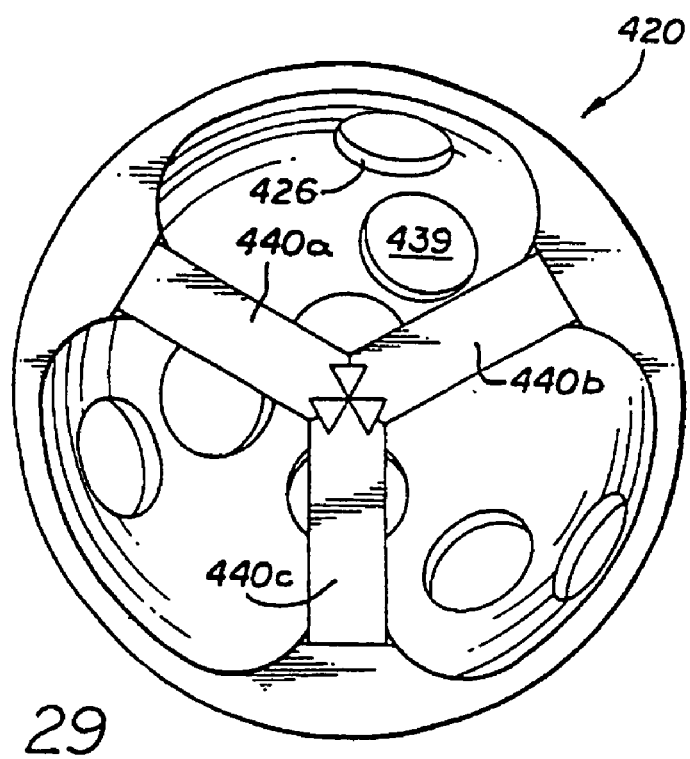
FIG. 29 is a bottom view of the underside of a reamer having an alternative triangular array of peripherally emanating mounting bars of the invention.

As shown in FIG. 29, the mounting bars 440a-c may alternatively meet centrally, as where a recessed driver connection is desired, as explained below.

It will be appreciated that, although the various mounting bar configurations described above in FIGS. 25-29 are depicted without the removable cutting teeth 422 shown in FIGS. 30-32 below, it is preferred that the apertures 426 which define the cutting sites have the removable teeth of the present invention.

The driver 444 represented in FIGS. 30-32 comprises a shank 446 with a shoulder 448, and a spindle head generally indicated at 450. Head 450 further comprises a slide 452 mounted about a shaft 454, one end 456 of which is fixed to the shank 446 and the other end of which is provided with a flange 458 having a diameter greater than that of the shaft 454. The slide 452 is pushed on the shaft 454 axially in the direction of arrow 460 by a spring (not shown) which applies it against the upper flange 462 of the shaft. The upper flange 458 serves as bayonet, preferably having a protrusion 464 at its center thus forming a collar shape. Formed in this collar are four L-shaped bayonet catches 466 which are intended to receive the mounting bar 440 of the reamer. The slide 452 is provided with four studs 468 which are parallel to the shaft 454 and to which there correspond four holes 470 (FIG. 32) in the flange 462, the studs passing through these holes in order to close the catches 446 of the bayonet and thus lock the mounting bar 440 of the reamer in the head 450 of the spindle shaft 454. In order to unlock the mounting bar 440, slide 452 is moved in a direction away from the flange 462 (opposite the direction of arrow 460) so that mounting bar 440 is no longer blocked in the catches 446 of the bayonet by the studs 470. This allows the driver 444 to be disassembled from the reamer 420.

As shown in FIGS. 27-29, greater number and a different array of mounting bars can be provided as described above, in which case the number and location of the bayonet catches would need to be correspondingly structured and arrayed so as to accommodate the particular choice of design, respectively. Those skilled in the art will appreciate the manner in which the catches could be provided to adapt them to receive whatever number and array is intended by the user, according to the teachings of the present invention.

Protrusion 464 could be stationary or spring-loaded, however, in use with a reamer 420 of the type shown in either FIGS. 25-28 the protrusion functions as a centering means allowing for greater ease of effecting the bayonet connection between driver 444 and reamer 420. In the case where protrusion 464 functions as a centering means, for example, in conjunction with the single mounting bar 440 having aperture 442 within which it is received (FIGS. 30-32), the user experiences less effort and time finding the correct orientation needed for making the bayonet connection. This is important in minimizing the surgeon's time in performing the bone preparation steps of the given implantation procedure. The single mounting bar 440 (FIGS. 25-26 and 30-32) may be captured by the bayonet connection in any opposed pair of the (four) catches 466 due to its relatively simple orientation requirements. Where the protrusion is spring-loaded (not shown), this allows use of the same driver with the mounting bars 440a-c of FIG. 29 which meet centrally and require a recessed structure of the area between catches 466 internally of upper flange 462, as will be appreciated by those skilled in the art. Alternatively, where centrally meeting mounting bars 440a-c are employed, as in FIG. 29, the protrusion 464 could be eliminated altogether.

The structure of those reamers 420 shown by FIGS. 25-29 yield further improvements in the ease and speed by which removed bone matter can, in turn, be emptied from the cavity 434 within which it has been captured, for later reuse by the surgeon in the implantation procedure. This is because the underside of the base 432 of reamer 420 is more open and thus accessible to the surgeon's extrication.

The entire reamer 420, exclusive of removable and replaceable teeth 422, can be cast, molded or stamped. Where a molding operation is used, the mounting bar 440 and armatures 441 (FIGS. 25-26) can be molded in the same operation as the wall of reamer 420, thus reducing the number of components and steps needed to fabricate the reamer.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A rotary surgical reamer, comprising:
   a) a hollow reamer body having a wall with an external surface and a base, the wall defining a central cavity and a plurality of passageways through the wall defining cutting sites, the passageways communicating between the external surface of the wall and the central cavity for passage of removed bone and tissue through the wall into the central cavity; and
   b) a retaining bar having a length extending along a longitudinal axis of the bar to spaced apart terminal ends permanently attached to a periphery of the base, wherein the retaining bar comprises spaced apart first and second retaining bar sides extending to the base periphery and located on opposite sides of the longitudinal axis of the retaining bar and a central retaining bar structure substantially centered between where the opposed ends of the retaining bar attach to the base periphery, the central retaining bar structure having opposed first and second radiused sides extending beyond respective planes of the first and second retaining bar sides, the opposed first and second radiused sides being aligned with each other along a perpendicular axis bisecting the longitudinal axis of the retaining bar.

2. The rotary surgical reamer of claim 1 being connectable to a shaft provided for transmitting torque about a central axis of the shaft, thereby providing for rotation of the reamer body.

3. The rotary surgical reamer of claim 1 wherein a width of the retaining bar is defined by arc segments of the base periphery where the respective first and second terminal ends of the retaining bar attach thereto.

4. The rotary surgical reamer of claim 1 wherein the terminal ends are affixed to a back side of the periphery.

5. The rotary surgical reamer of claim 1 wherein the retaining bar has a considerably flat configuration.

6. The rotary surgical reamer of claim 1 wherein the base further comprises a periphery and the retaining bar is an integral bar attached to the periphery of the base.

7. The rotary surgical reamer of claim 1 further comprising closure means adapted to be secured to the base for transmitting torque from a shaft to the reamer body while keeping the removed bone and tissue contained in the central cavity.

8. A rotary surgical reamer, comprising:
   a) a hollow reamer body having a wall with an external surface and a base having a periphery, the wall defining a central cavity and a plurality of passageways through the wall defining cutting sites, the passageways communicating between the external surface of the wall and the central cavity for passage of removed bone and tissue through the wall into the central cavity; and
   b) a retaining bar permanently attached to the periphery of the base, the retaining bar comprising a first width and a length with the opposed ends attached to the base, and a generally round structure with a second diameter centered on a length of the bar at an axis of rotation wherein the second diameter is greater than the first width.

9. The rotary surgical reamer of claim 8 further comprising closure means adapted to be secured to the base for transmitting torque from a shaft to the reamer body while keeping the removed bone and tissue contained in the central cavity.

10. A rotary surgical reamer, comprising:
    a) a hollow reamer body having a wall with an external surface, a base and a cutter axis, the wall defining a central cavity and a plurality of passageways through the wall defining cutting sites, the passageways communicating between the external surface of the wall and the central cavity for passage of removed bone and tissue through the wall into the central cavity; and
    b) a retaining bar extending along a longitudinal axis of the bar across the periphery of the base, the retaining bar permanently attached to the periphery of the base and comprising a radiused structure with a first cross section centered on an axis of rotation of the reamer body, the retaining bar having a second cross section perpendicular to the longitudinal axis of the bar that is less than the first cross section.

\* \* \* \* \*